US012655168B2

(12) United States Patent
Galaev et al.

(10) Patent No.: US 12,655,168 B2
(45) Date of Patent: Jun. 16, 2026

(54) ISOLATION OF STEVIOL GLYCOSIDES

(71) Applicant: DSM IP ASSETS B.V., Heerlen (NL)

(72) Inventors: Igor Galaev, Echt (NL); Ferdinand Antoine Spros, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 1073 days.

(21) Appl. No.: 17/765,644

(22) PCT Filed: Oct. 15, 2020

(86) PCT No.: PCT/EP2020/079128
§ 371 (c)(1),
(2) Date: Mar. 31, 2022

(87) PCT Pub. No.: WO2021/074344
PCT Pub. Date: Apr. 22, 2021

(65) Prior Publication Data
US 2022/0389043 A1 Dec. 8, 2022

(30) Foreign Application Priority Data
Oct. 17, 2019 (EP) ..................................... 19203923

(51) Int. Cl.
| | |
|---|---|
| *C07H 1/06* | (2006.01) |
| *A23L 27/30* | (2016.01) |
| *C07H 15/256* | (2006.01) |
| *C12N 9/02* | (2006.01) |
| *C12N 9/10* | (2006.01) |
| *C12N 15/82* | (2006.01) |

(52) U.S. Cl.
CPC ................ *C07H 1/06* (2013.01); *A23L 27/36* (2016.08); *C07H 15/256* (2013.01); *C12N 9/0042* (2013.01); *C12N 9/1048* (2013.01); *C12N 15/8243* (2013.01)

(58) Field of Classification Search
CPC ................................. C07H 1/06; C12N 9/1048
See application file for complete search history.

(56) References Cited

U.S. PATENT DOCUMENTS

| | | | |
|---|---|---|---|
| 9,518,118 B2 | 12/2016 | Chen et al. | |
| 10,604,743 B2 | 3/2020 | Boer et al. | |
| 10,689,410 B2 | 6/2020 | Galaev et al. | |
| 10,947,515 B2 | 3/2021 | Boer et al. | |
| 11,066,688 B2 | 7/2021 | Geertman et al. | |
| 11,104,886 B2 | 8/2021 | Van Leeuwen et al. | |
| 11,117,916 B2 | 9/2021 | Galaev et al. | |
| 11,124,535 B2 | 9/2021 | Geertman et al. | |
| 11,459,548 B2 | 10/2022 | Boer et al. | |
| 2015/0031868 A1 | 1/2015 | Lehmann et al. | |
| 2016/0153017 A1 | 6/2016 | Van Der Hoeven | |
| 2016/0185813 A1 | 6/2016 | Galaev et al. | |
| 2018/0057850 A1 | 3/2018 | Bosch et al. | |
| 2018/0163244 A1* | 6/2018 | Anderson | C12P 19/56 |
| 2019/0169220 A1 | 6/2019 | Galaev et al. | |
| 2019/0194240 A1 | 6/2019 | Galaev et al. | |
| 2021/0310034 A1 | 10/2021 | Geertman et al. | |
| 2021/0348136 A1 | 11/2021 | Van Leeuwen et al. | |
| 2021/0371445 A1 | 12/2021 | Geertman et al. | |

FOREIGN PATENT DOCUMENTS

| | | |
|---|---|---|
| NO | 2018029272 A1 | 2/2018 |
| WO | 2011153378 A1 | 12/2011 |
| WO | 2013022989 A2 | 2/2013 |
| WO | 2013/110673 A1 | 8/2013 |
| WO | 2014122227 A2 | 8/2014 |
| WO | 2015007748 A1 | 1/2015 |
| WO | 2015014959 A1 | 2/2015 |
| WO | 2016/100689 A1 | 6/2016 |
| WO | 2016146711 A1 | 9/2016 |
| WO | 2016151046 A1 | 9/2016 |
| WO | 2016/196345 A1 | 12/2016 |
| WO | 2017009293 A1 | 1/2017 |
| WO | 2017009294 A1 | 1/2017 |
| WO | 2018029274 A1 | 2/2018 |
| WO | 2018104238 A1 | 6/2018 |
| WO | 2019/071254 A1 | 4/2019 |

OTHER PUBLICATIONS

Jinping Dong et al., "Characterization of a new hemihydrate rebaudioside B crystal having lower aqueous solubility", Food Chemistry, vol. 304, pp. 1-8 Aug. 29, 2019 (Abstract only provided).
International Search Report received in application No. PCT/EP2020/079128, mailed Jan. 21, 2021, 3 pages.
Dong et al., "Characterization of a new hemihydrate reaudioside B crystal having lower aqueous solubility," Food Chemistry, ElSeiver Ltd., NL, vol. 304, No. 29, p. 125444, 2020, pp. 1-7.
Humphrey et al., "Spatial organisation of four enzymes from Stevia rebaudiana that are involved in steviol glycoside synthesis," Plant Molecular Biology, 2006, 61: 47-62.
Mohamed et al., "UDP-dependent glycosyltransferases involved in the biosynthesis of steviol glycosides," Journal of Plant Physiology, 2011, 168: 1136-1141.

* cited by examiner

*Primary Examiner* — Ruth A Davis
(74) *Attorney, Agent, or Firm* — McBee, Moore & Vanik IP, LLC

(57) ABSTRACT

The disclosure relates to the field of food ingredients, specifically to sweeteners, more specifically to steviol glycosides and improved isolation thereof.

17 Claims, 1 Drawing Sheet

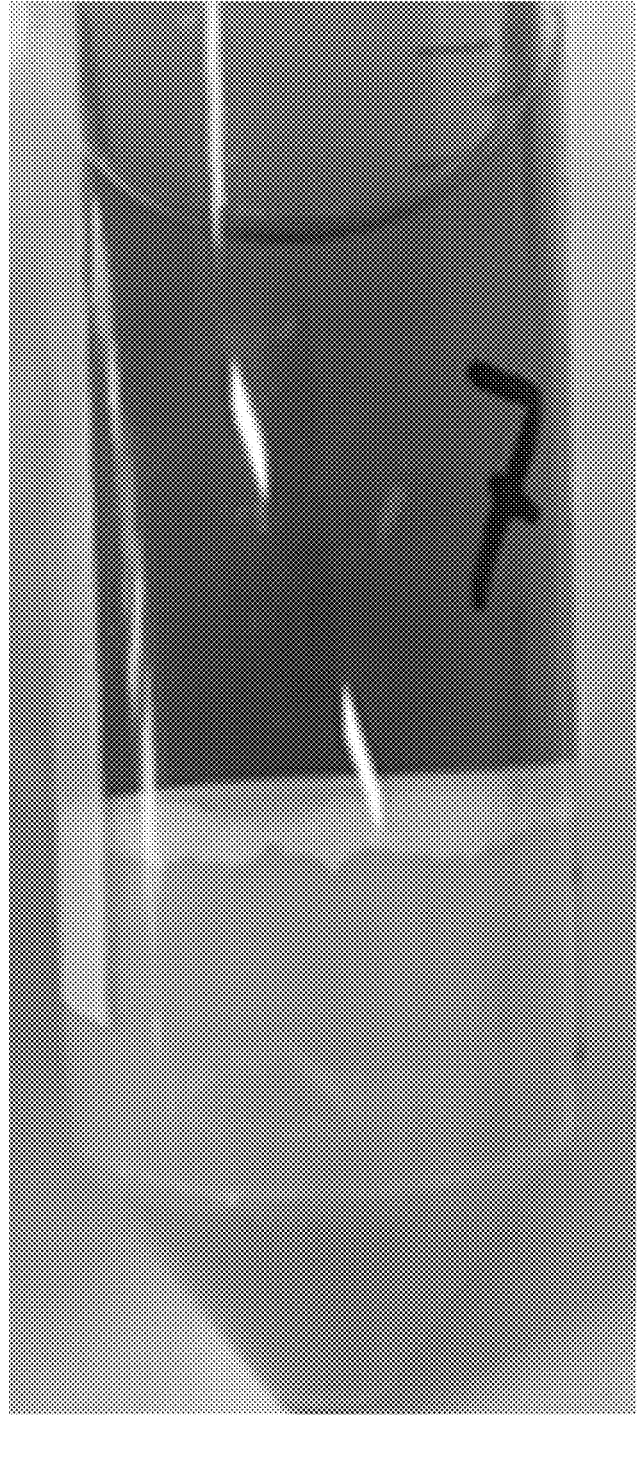

ISOLATION OF STEVIOL GLYCOSIDES

CROSS-REFERENCE TO RELATED APPLICATIONS

This application is the National Stage entry of International Application No. PCT/EP2020/079128, filed 15 Oct. 2020, which claims priority to European Patent Application No. 19203923.8, filed 17 Oct. 2019.

BACKGROUND

Field

The disclosure relates to the field of food ingredients, specifically to sweeteners, more specifically to steviol glycosides and improved isolation thereof.

The leaves of the perennial herb, *Stevia rebaudiana* Bertoni, accumulate quantities of intensely sweet compounds known as steviol glycosides. Whilst the biological function of these compounds is unclear, they have commercial significance as alternative high potency sweeteners. These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M (Reb M) is a further high-potency diterpene glycoside sweetener. It is present in trace amounts in certain *stevia* variety leaves but has been suggested to have a superior taste profile if compared to the other steviol glycosides. In particular, rebaudioside M seems to be lacking the bitter, liquorice after-taste which is typical of other steviol glycosides, in particular rebaudioside A.

Steviol glycosides have traditionally been extracted from the *Stevia* plant. In *Stevia*, (−)-kaurenoic acid, an intermediate in gibberellic acid (GA) biosynthesis, is converted into the tetracyclic diterpene steviol, which then proceeds through a multi-step glycosylation pathway to form the various steviol glycosides.

In *Stevia* plants yields may be variable and affected by agriculture and environmental conditions. Furthermore, Rebaudioside D and rebaudioside M, which have an improved sweetness and sensory profile if compared with rebaudioside A, are present only in traces in plant extracts.

DESCRIPTION OF RELATED ART

As a consequence, more recently, interest has grown in producing steviol glycosides using fermentative processes. WO2013/110673 and WO2015/007748 describe microorganisms that may be used to produce at least the steviol glycosides such as rebaudioside A, rebaudioside D and rebaudioside M. Rebaudioside M is available in various *stevia* compositions, whether obtained from *Stevia* leaves or by fermentation (see e.g. WO2015007748).

The limited solubility of steviol glycosides, especially of rebaudioside M, can be problematic during fermentation of recombinant cells suitably transformed to produce such steviol glycosides and isolation can be impaired since precipitated steviol glycosides will mix with the recombinant cells, especially during centrifugation to separate the cells from the supernatant comprising the steviol glycosides.

Dong and Yang ("Characterization of a new hemihydrate rebaudioside B crystal having lower aqueous solubility", FOOD CHEMISTRY, ELSEVIER LTD, NL, vol. 304, 125444, 29 Aug. 2019) describe the isolation of a new hemihydrate crystal form of rebaudioside B with a solubility in water as low as 50 ppm. This new crystal form was obtained after heating to dissolve and subsequently cooling down a 0.06% reb B solution to room temperature.

WO2016/100689 A1 disclose four new steviol glycosides comprising 7 or 8 sugar moieties, wherein said steviol glycosides comprise a branched chain of four sugar units attached to the carbon in position 13 of the steviol backbone via a glycosidic bond. The presence of compound 1 to 4, even at low concentration, showed a positive influence on the aqueous solubility of reb D and reb M in a composition.

There is thus an urge to improve the isolation of steviol glycosides produced by fermentation, especially of rebaudioside M.

DETAILED DESCRIPTION OF A PREFERRED EMBODIMENT

FIG. 1 depicts a white layer of steviol glycoside crystals on top of the cells after centrifugation.

SUMMARY

The disclosure relates to a process for the production of one or more steviol glycosides, wherein a recombinant cell capable of producing one or more steviol glycosides is cultured in a suitable culture medium under conditions wherein said one or more steviol glycosides are produced and wherein one or more steviol glycosides precipitate out of the culture broth, comprising treating the culture broth such that the precipitated one or more steviol glycosides are at least partially re-solubilized, preferably wherein substantially all of the one or more steviol glycosides are re-solubilized.

DETAILED DESCRIPTION

In a first aspect, the disclosure provides for a process for the production of one or more steviol glycosides, wherein a recombinant cell capable of producing one or more steviol glycosides is cultured in a suitable culture medium under conditions wherein said one or more steviol glycosides are produced and wherein one or more steviol glycosides precipitate out of the culture broth, comprising treating the culture broth such that the precipitated one or more steviol glycosides are at least partially re-solubilized in the culture broth, preferably wherein substantially all of the one or more steviol glycosides are re-solubilized in the culture broth.

In this aspect, there is also provided for a process for the recovery of one or more steviol glycosides from a culture broth wherein said culture broth comprises recombinant cells capable of producing one or more steviol glycosides, a culture medium, one or more precipitated steviol glycosides and optionally one or more solubilised steviol glycosides, wherein the process comprises treating the culture broth such that the precipitated one or more steviol glycosides are at least partially re-solubilized in the culture broth, preferably wherein substantially all of the one or more steviol glycosides are re-solubilized in the culture broth. Effectively, the one or more steviol glycosides may be recovered from the culture broth after their partial or complete re-solubilisation.

In the embodiments of the disclosure, the steviol glycoside is preferably produced by fermentation in a recombinant cell. Alternatively, the steviol glycoside can be produced by whole cell bioconversion.

Therefore there is also provided a process for the production of one or more steviol glycosides wherein a recombinant cell capable of producing one or more steviol glycosides starting from one or more steviol glycoside substrate (e.g. a steviol glycoside extract of plant origin, rebaudioside A, stevioside, or a mixture thereof, etcetera) is cultured in a suitable culture medium under conditions wherein said one or more steviol glycosides substrate are further glycosylated by the cell, to yield said one steviol glycosides and wherein said one or more steviol glycosides precipitate out of the culture broth, comprising treating the culture broth such that the precipitated one or more steviol glycosides are at least partially re-solubilized in the culture broth, preferably wherein substantially all of the one or more steviol glycosides are re-solubilized in the culture broth.

There is also provided a process for the recovery of one or more steviol glycosides from a culture broth wherein said culture broth comprises recombinant cells capable of producing one or more steviol glycosides starting from one or more steviol glycoside substrate (e.g. a steviol glycoside extract of plant origin, rebaudioside A, stevioside, or a mixture thereof, etcetera), a culture medium, one or more precipitated steviol glycosides, and optionally one or more solubilised steviol glycosides, wherein the process comprises treating the culture broth such that the precipitated one or more steviol glycosides are at least partially re-solubilized in the culture broth, preferably wherein substantially all of the one or more steviol glycosides are re-solubilized in the culture broth.

Processes for the production of steviol glycosides by fermentation or bioconversion of recombinant cells are known to the person skilled in the art and are e.g. described in WO2011153378, WO2013022989, WO2013110673, WO2014122227, WO2015007748.

In the context of the disclosure "culture broth", "fermentation broth", or "fermentation liquid" may be used interchangeably. A culture broth typically comprises culture medium, the recombinant cell of the disclosure and optionally the product produced by the recombinant cell, e.g. the steviol glycosides. Treatment of the culture broth to re-solubilize the precipitated one or more steviol glycoside can be performed in any way known to the person skilled in the art; a preferred treatment is any described throughout the specification and in the examples herein.

In the embodiments of the disclosure, the re-solubilisation of the one or more steviol glycosides may occur under conditions wherein lysis of the recombinant cells in the culture broth is substantially prevented. Substantially prevented is herein construed as that at most 10%, preferably at most 5%, more preferably at most 4%, 3%, 3%, 2%, 1%, 0.5%, 0.4%, 0.3%, 0.2%, 0.1%, 0.05%, or at most 0.01% of the recombinant cells is lysed. Lysis of recombinant cells can be determined by any means known to the person skilled in the art. A preferred means is the method described in the examples herein wherein an increase the amount of dry matter is determined (dry matter being cellular components) or wherein an increase in cell pellet is determined.

In the embodiments of the disclosure, the re-solubilisation of the one or more steviol glycosides may be performed by subjecting the culture broth comprising the recombinant cells and the precipitated one or more steviol glycosides (and optionally one or more solubilised steviol glycosides) to a heating step. When in the embodiment of the disclosure, a heating step is performed for re-solubilisation of the one or more steviol glycosides, the heating step may be performed at a temperature and for a period of time under which the one or more steviol glycosides are at least partially re-solubilised in the culture broth, preferably under conditions wherein the one or more steviol glycosides are completely re-solubilised in the culture medium. The term "partially re-solubilised" is herein construed as that at most 10%, 20%, 30%, 40%, 50%, 60%, 70%, 80%, 90%, 91%, 92%, 93%, 94%, 95%, 96%, 97%, 98%, or at least 99% of the one or more steviol glycosides are re-solubilised in the culture medium.

In an embodiment, the heating step is performed at a temperature comprised between 45-75° C. and/or for a period of time of at most about 90 seconds. In an embodiment, the heating step is performed at either 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90° C. for a period of time of at most 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 or 90 seconds.

In an embodiment, the heating step is performed at a temperature of 55-70° C. and for a period of time of at most 60 seconds, particularly wherein the heating step is performed at a temperature of 60-70° C. and for a period of time of at most 60 seconds. In an embodiment, the heating step is performed at either 55, 56, 57, 58, 59, 60, 61, 62, 63, 64, 65, 66, 67, 68, 69 or 70° C. for a period of time of at most 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 seconds. In an embodiment, the heating step is performed at 55, 56, 57, 58, 59, 60, 61, 62, 63, 64, 65, 66, 67, 68, 69 or 70° C. for 25 seconds. In an embodiment, the heating step is performed at 55, 56, 57, 58, 59, 60, 61, 62, 63, 64, 65, 66, 67, 68, 69 or 70° C. for 26 seconds. In an embodiment, the heating step is performed at 55, 56, 57, 58, 59, 60, 61, 62, 63, 64, 65, 66, 67, 68, 69 or 70° C. for 27 seconds. In an embodiment, the heating step is performed at 55, 56, 57, 58, 59, 60, 61, 62, 63, 64, 65, 66, 67, 68, 69 or 70° C. for 28 seconds. In an embodiment, the heating step is performed at 55, 56, 57, 58, 59, 60, 61, 62, 63, 64, 65, 66, 67, 68, 69 or 70° C. for 29 seconds. In an embodiment, the heating step is performed at 55, 56, 57, 58, 59, 60, 61, 62, 63, 64, 65, 66, 67, 68, 69 or 70° C. for 30 seconds. In an embodiment, the heating step is performed at 55, 56, 57, 58, 59, 60, 61, 62, 63, 64, 65, 66, 67, 68, 69 or 70° C. for 31 seconds. In an embodiment, the heating step is performed at 55, 56, 57, 58, 59, 60, 61, 62, 63, 64, 65, 66, 67, 68, 69 or 70° C. for 32 seconds. In an embodiment, the heating step is performed at 55, 56, 57, 58, 59, 60, 61, 62, 63, 64, 65, 66, 67, 68, 69 or 70° C. for 33 seconds. In an embodiment, the heating step is performed at 55, 56, 57, 58, 59, 60, 61, 62, 63, 64, 65, 66, 67, 68, 69 or 70° C. for 34 seconds. In an embodiment, the heating step is performed at 55, 56, 57, 58, 59, 60, 61, 62, 63, 64, 65, 66, 67, 68, 69 or 70° C. for 35 seconds. In an embodiment, the heating step is performed at 55, 56, 57, 58, 59, 60, 61, 62, 63, 64, 65, 66, 67, 68, 69 or 70° C. for 36 seconds. In an embodiment, the heating step is performed at 55, 56, 57, 58, 59, 60, 61, 62, 63, 64, 65, 66, 67, 68, 69 or 70° C. for 37 seconds. In an embodiment, the heating step is performed at 55, 56, 57, 58, 59, 60, 61, 62, 63, 64, 65, 66, 67, 68, 69 or 70° C. for 38 seconds. In an embodiment, the heating step is performed at 55, 56, 57, 58, 59, 60, 61, 62, 63, 64, 65, 66, 67, 68, 69 or 70° C. for 39 seconds. In an embodiment, the heating step is performed at 55, 56, 57, 58, 59, 60, 61, 62, 63, 64, 65, 66, 67, 68, 69 or 70° C. for 40 seconds. In an embodiment, the heating step is performed at 55, 56, 57, 58, 59, 60, 61, 62, 63, 64, 65, 66, 67, 68, 69 or 70° C. for 41 seconds. In an embodiment, the heating step is performed at 55, 56, 57, 58, 59, 60, 61, 62, 63, 64, 65, 66, 67, 68, 69 or 70° C. for 42 seconds. In an embodiment, the heating step is performed at 55, 56, 57, 58, 59, 60, 61, 62, 63, 64, 65, 66, 67, 68, 69 or 70° C. for 43 seconds. In an embodiment, the heating step is performed at 55, 56, 57, 58, 59, 60, 61, 62, 63, 64, 65, 66, 67, 68, 69 or 70° C. for 44 seconds. In an embodiment, the heating step is performed at 55, 56, 57, 58, 59, 60, 61, 62, 63, 64, 65, 66, 67, 68, 69 or 70° C. for 45 seconds. In an embodiment, the heating step is performed at 55, 56, 57, 58, 59, 60, 61, 62, 63, 64, 65, 66, 67, 68, 69 or 70° C. for 46 seconds. In an embodiment, the heating step is performed at 55, 56, 57, 58, 59, 60, 61, 62, 63, 64, 65, 66, 67, 68, 69 or 70° C. for 47 seconds. In an embodiment, the heating step is performed at 55, 56, 57, 58, 59, 60, 61, 62, 63, 64, 65, 66, 67, 68, 69 or 70° C. for 48 seconds. In an embodiment, the heating step is performed at 55, 56, 57, 58, 59, 60, 61, 62, 63, 64, 65, 66, 67, 68, 69 or 70° C. for 49 seconds. In an embodiment, the heating step is performed at 55, 56, 57, 58, 59, 60, 61, 62, 63, 64, 65, 66, 67, 68, 69 or 70° C. for 50 seconds. In an embodiment, the heating step is performed at 55, 56, 57, 58, 59, 60, 61, 62, 63, 64, 65, 66, 67, 68, 69 or 70° C. for 51 seconds. In an embodiment, the heating step is performed at 55, 56, 57, 58, 59, 60, 61, 62, 63, 64, 65, 66, 67, 68, 69 or 70° C. for 52 seconds. In an embodiment, the heating step is performed at 55, 56, 57, 58, 59, 60, 61, 62, 63, 64, 65, 66, 67, 68, 69 or 70° C. for 53 seconds. In an embodiment, the heating step is performed at 55, 56, 57, 58, 59, 60, 61, 62, 63, 64, 65, 66, 67, 68, 69 or 70° C. for 54 seconds. In an embodiment, the heating step is performed at 55, 56, 57, 58, 59, 60, 61, 62, 63, 64, 65, 66, 67, 68, 69 or 70° C. for 55 seconds. In an embodiment, the heating step is performed at 55, 56, 57, 58, 59, 60, 61, 62, 63, 64, 65, 66, 67, 68, 69 or 70° C. for 56 seconds. In an embodiment, the heating step is performed at 55, 56, 57, 58, 59, 60, 61, 62, 63, 64, 65, 66, 67, 68, 69 or 70° C. for 57 seconds. In an embodiment, the heating step is performed at 55, 56, 57, 58, 59, 60, 61, 62, 63, 64, 65, 66, 67, 68, 69 or 70° C. for 58 seconds. In an embodiment, the heating step is performed at 55, 56, 57, 58, 59, 60, 61, 62, 63, 64, 65, 66, 67, 68, 69 or 70° C. for 59 seconds. In an embodiment, the heating step is performed at 55, 56, 57, 58, 59, 60, 61, 62, 63, 64, 65, 66, 67, 68, 69 or 70° C. for 60 seconds.

In the embodiments of the disclosure, the heating step may be performed using any means known to the person skilled in the art, such as using a heat plate exchanger.

In the embodiments of the disclosure, the one or more steviol glycosides present in the culture broth may be recovered and optionally purified. Recovery and purification may be performed using any means known to the person skilled in the art. The process of the disclosure may further comprise removal of the recombinant cells from the culture broth. Removal of the recombinant cells from the culture broth may be performed using any means known to the person skilled in the art; the one or more steviol glycosides present in the culture medium may be separated from the recombinant cells by centrifugation. In an embodiment, the centrifuge is operably linked to the heat plate exchanger.

In an embodiment, the one or more steviol glycosides present in the culture medium are separated from the recombinant cells by centrifugation at most 40,000 g*minute, and centrifugation time is preferably at most 5 minutes. In an embodiment, g*t is between 10,000 and 30,000 g*min, such as between 15000 to 20 000 g*min.

In the embodiments of the disclosure, recovery and optional purification of said one or more steviol glycosides may comprise or may further comprise one or more of a filtration step, ultra-filtration step, evaporation step, a crystallisation step and a heat shock step of the culture medium (i.e. the culture broth no longer comprising the recombinant cells). Methods to recover and purify steviol glycosides, such as to recover and purify steviol glycosides produced by fermentation, have been described in e.g. WO2015/014959 A1, WO2017/009293 A1, WO2017/009294 A1, WO2018/029272 A1 and WO2018/029274 A1.

In the embodiments of the disclosure, the one or more steviol glycosides may be any steviol glycoside. In an embodiment, the one or more steviol glycosides is reb M, reb D, reb A or a composition thereof. The abbreviation "reb" is known to the person skilled in the art as rebaudioside; accordingly, rebM means Rebaudioside M.

Typically, a recombinant cell which can be used in a method according to the disclosure is capable of producing a glycosylated diterpene, such as a steviol glycoside. For example, a recombinant cell according to the disclosure may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebaudioside A, rebaudioside E, rebaudioside I, rebaudioside G, rebaudioside D or rebaudioside M. Typically the recombinant cell is capable of producing rebaudioside M; and/or other steviol glycosides, such as one or more of rebaudioside A, rebaudioside B, rebaudioside D, rebaudioside I, rebaudioside G, stevioside, steviolbioside, rubusoside, and steviol-13-monoside.

A recombinant cell according to the disclosure may comprise one or more recombinant nucleic acid sequences encoding one or more polypeptides having UDP-glycosyltransferase (UGT) activity.

For the purposes of this disclosure, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 3 sets out a schematic diagram of steviol glycoside formation.

A recombinant cell according to the disclosure may thus comprise one or more recombinant nucleic acid sequences encoding:

(i) a polypeptide having UGT74G1 activity;
(ii) a polypeptide having UGT2 activity;
(ii) a polypeptide having UGT85C2 activity; and
(iii) a polypeptide having UGT76G1 activity.

A recombinant cell suitable for use in the in the production of steviol glycosides may comprise a nucleotide sequence encoding a polypeptide capable of catalysing the addition of a C-13-glucose to steviol. That is to say, a recombinant yeast suitable for use in a method of the disclosure may comprise a UGT which is capable of catalyzing a reaction in which steviol is converted to steviol monoside.

Such a recombinant cell suitable for use in the production of steviol glycosides may comprise a nucleotide sequence encoding a polypeptide having the activity shown by UDP-glycosyltransferase (UGT) UGT85C2, whereby the nucleotide sequence upon transformation of the yeast confers on that yeast the ability to convert steviol to steviol monoside.

UGT85C2 activity is transfer of a glucose unit to the 13-OH of steviol.

Thus, a suitable UGT85C2 may function as a uridine 5'-diphospho glucosyl: steviol 13-OH transferase, and a uridine 5'-diphospho glucosyl: steviol-19-O-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein. Therefore a UGT1 polypeptide (or polypeptide having UGT1 activity) is capable of glycosylating steviol or a precursor steviol glycoside at a C-13 hydroxyl group present in said steviol or precursor steviol glycoside, preferably wherein the glycosylation is a beta-glycosylation.

A recombinant cell suitable for use in the disclosure may comprise a nucleotide sequence encoding a polypeptide which has UGT2 activity. A polypeptide with UGT2 activity is a polypeptide capable of 1,2 glycosylation (preferably beta 1,2-glycosylation) of the C2' of the 13-O-glucose, of the 19-O-glucose or both the 13-O-glucose and the 19-O-glucose of a precursor steviol glycoside having a 13-O-glucose, a 19-O-glucose, or both the 13-O-glucose and the 19-O-glucose.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-O-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide typically does not transfer a glucose moiety to steviol compounds having a 1,3-bound glucose at the C-13 position, i.e., transfer of a glucose moiety to steviol 1,3-bioside and 1,3-stevioside typically does not occur. A polypeptide having UGT2 activity may encompass a UGT2 polypeptide which preferentially catalyzes conversion of steviol-13-monoside to steviolbioside and/or conversion of rubusoside to stevioside which may help to steer production towards rebaudioside A. Alternatively, a polypeptide having UGT2 activity may encompass a UGT2 polypeptide which preferentially catalyzes conversion of stevioside to rebaudioside E or rubusoside to a compound with an additional sugar at the 19 position which may help to steer production towards rebaudioside M. That is to say preference for addition of a sugar moiety at the 13 position may help steer production towards rebaudioside A, whereas preference for addition of a sugar moiety at the 19 position may help steer production towards rebaudioside M. Examples of specific UGT2 are those described in SEQ ID NO: 1, 3, 6, 9, 11, 14, 17, 20, 22 or 25 of WO2016146711. Other UGT2 are described in SEQ ID NO: 1, 2, 3 and 4 of WO2016151046.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl: steviol-13-O-glucoside transferase, transferring a rhamnose moiety to the C-2' of the 13-O-glucose of the acceptor molecule, steviol.

A recombinant cell suitable for use in the method of production of steviol glycosides according to the disclosure may comprise a nucleotide sequence encoding a polypeptide having UGT activity may comprise a nucleotide sequence encoding a polypeptide capable of catalyzing the addition of a C-19-glucose to steviolbioside. That is to say, a recombinant yeast of the disclosure may comprise a UGT which is capable of catalyzing a reaction in which steviolbioside is converted to stevioside. Accordingly, such a recombinant yeast may be capable of converting steviolbioside to stevioside. Expression of such a nucleotide sequence may confer on the recombinant yeast the ability to produce at least stevioside.

A recombinant cell suitable for use in the method of production of steviol glycosides according to the disclosure may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH or the 19-COOH of steviol. A suitable UGT74G1 polypeptide may function as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences. Therefore a polypeptide with UGT3 activity is a polypeptide capable of glycosylating steviol or a precursor steviol glycoside at a C-19 carboxyl group present in said steviol or precursor steviol glycoside, preferably wherein the glycosylation is a beta-glycosylation.

A recombinant cell suitable for use in the method of production of steviol glycosides according to the disclosure may comprise a nucleotide sequence encoding a polypeptide capable of catalyzing glucosylation of the C-3' of the glucose at the C-13 position of stevioside. That is to say, a recombinant yeast suitable for use in a method of the disclosure may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

A recombinant cell suitable for use in the method of production of steviol glycosides according to the disclosure may thus also comprise a nucleotide sequence encoding a polypeptide having the activity shown by UDP-glycosyl-transferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM. Therefore a polypeptide having UGT4 activity Is capable of 1,3 glycosylation, preferably beta 1,3-glycosylation, of the C3' of a 13-O-glucose, of a 19-O-glucose or both the 13-O-glucose and the 19-O-glucose of a precursor steviol glycoside having a 13-O-glucose, a 19-O-glucose, or both a 13-O-glucose and a 19-O-glucose.

A recombinant cell according to the disclosure for use in the production of one or more steviol glycosides wherein a recombinant cell is capable of producing one or more steviol glycosides starting from one or more steviol glycoside substrate (e.g. a steviol glycoside extract of plant origin, rebaudioside A, stevioside, or any mixture of one or more glycosides as described herein before) typically comprises nucleotide sequences encoding at least one or more polypeptide having UGT activity, such as UGT1 activity, UGT2 activity, UGT3 activity and/or UGT4 activity.

A recombinant cell for use in the method of production of steviol glycosides according to the disclosure, wherein a recombinant cell is capable of producing one or more steviol glycosides when cultured in a suitable culture medium under conditions wherein said one or more steviol glycosides are produced (i.e. fermentative production of steviol glycosides) typically comprises nucleotide sequences encoding at least one polypeptide having UGT1 activity, at least one polypeptide having UGT2 activity, at least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid may encode a polypeptide which has two, three or four of the activities set out above. Preferably, a recombinant yeast for use in the method of the disclosure comprises UGT1, UGT2 and UGT3 and UGT4 activity. Suitable UGT1, UGT2, UGT3 and UGT4 sequences are described in Table 1 of WO2015/007748.

A recombinant cell according to the disclosure may comprise two or more nucleic acid sequences encoding a polypeptide having any one UGT activity, for example UGT, 2, 3 or 4, activity. Where a recombinant cell according to the disclosure comprises two or more nucleic acid sequence encoding a polypeptide having any one UGT activity, those nucleic acid sequences may be the same or different and/or may encode the same or different polypeptides. In particular, a recombinant cell according to the disclosure may comprise a nucleic acid sequence encoding a two different UGT2 polypeptides.

A recombinant cell according to the disclosure may comprise one or more recombinant nucleotide sequence(s) encoding one of more of:

a polypeptide having ent-copalyl pyrophosphate synthase activity;

a polypeptide having ent-Kaurene synthase activity; and a polypeptide having ent-Kaurene oxidase activity.

A recombinant cell according to the disclosure may comprise a recombinant nucleotide sequence encoding a polypeptide having kaurenoic acid 13-hydroxylase activity.

For the purposes of this disclosure, a polypeptide having ent-copalyl pyrophosphate synthase (EC 5.5.1.13) is capable of catalyzing the chemical reaction:

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this disclosure, a polypeptide having ent-kaurene synthase activity (EC 4.2.3.19) is a polypeptide that is capable of catalyzing the chemical reaction:

ent-copalyl diphosphate ent-kaurene+diphosphate

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-Copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in a recombinant cell according to the disclosure may encode a polypeptide having ent-copalyl pyrophosphate synthase activity and ent-kaurene synthase activity. Alternatively, the two activities may be encoded two distinct, separate nucleotide sequences.

For the purposes of this disclosure, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

Suitable nucleic acid sequences encoding a kaurenoic acid 13-hydroxylase, may for instance comprise a sequence as set out in SEQ ID. NO: 27, 29, 31, 33, 69, 89, 91, 93, 95, 97, 146, 164, 165, 166, 167 or 185 of WO2015/007748. Other suitable kaurenoic acid 13-hydroxylases are the variant polypeptide described in WO2017/060318 or in WO2018/104238.

A recombinant cell according to the disclosure may comprise a recombinant nucleic acid sequence encoding a polypeptide having cytochrome p450 reductase activity as disclosed herein (CPR). That is to say, a recombinant cell according to the disclosure may be capable of expressing a nucleotide sequence encoding a polypeptide having cytochrome p450 reductase activity.

In a recombinant cell according to the disclosure, the ability of the recombinant cell to produce geranylgeranyl diphosphate (GGPP) may be upregulated. Upregulated in the context of this disclosure implies that the recombinant cell produces more GGPP than an equivalent non-recombinant cell.

Accordingly, a recombinant cell according to the disclosure may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of the microorganism confer(s) on the microorganism the ability to produce elevated levels of GGPP. Thus, a recombinant cell according to the disclosure may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant cell according to the disclosure may comprise nucleic acid sequences encoding one or more of:
- a polypeptide having hydroxymethylglutaryl-CoA reductase activity;
- a polypeptide having farnesyl-pyrophosphate synthetase activity;
- a polypeptide having geranylgeranyl diphosphate synthase activity.

In particular, it may be possible that the enzymes selected from the group consisting of ent-copalyl pyrophosphate synthase, ent-Kaurene synthase, ent-Kaurene oxidase, and kaurenoic acid 13-hydroxylase, UGTs, hydroxymethylglutaryl-CoA reductase, farnesyl-pyrophosphate synthetase, geranylgeranyl diphosphate synthase and cytochrome p450 reductase are native to the cell and that transformation with one or more of the nucleotide sequences encoding these enzymes may not be required to confer the cell the ability to produce steviol or a steviol glycoside. A preferred cell according to the present disclosure may be a recombinant cell which is naturally capable of producing GGPP (i.e. in its non-recombinant form).

Further improvement of steviol or steviol glycoside production by the cell or recombinant cell may be obtained by classical strain improvement.

In the embodiments of the disclosure, the recombinant cell may be a recombinant cell capable of producing steviol glycosides wherein said recombinant cell comprises one or more nucleic acid sequences encoding one or more of:
- a polypeptide having hydroxymethylglutaryl-CoA reductase activity;
- a polypeptide having farnesyl-pyrophosphate synthetase activity;
- a polypeptide having geranylgeranyl diphosphate synthase activity
- a polypeptide having ent-copalyl pyrophosphate synthase activity;
- a polypeptide having ent-Kaurene synthase activity;
- a polypeptide having ent-Kaurene oxidase activity;
- a polypeptide having kaurenoic acid 13-hydroxylase activity
- a polypeptide having NADPH-cytochrome p450 reductase activity
- a polypeptide having UGT74G1 activity;
- a polypeptide having UGT2 activity;
- a polypeptide having UGT85C2 activity;
- a polypeptide having UGT76G1 activity.

In the embodiments of the disclosure, the recombinant cell may be any microbial cell suitable for the production of one or more steviol glycosides. In an embodiment, the recombinant cell belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*, preferably the recombinant cell is a *Saccharomyces cerevisiae* cell, a *Yarrowia lipolytica* cell, a *Candida krusei* cell, an *Issatchenkia orientalis* cell or an *Escherichia coli* cell. In an embodiment, the recombinant cell is cell as defined in the General Definitions herein.

In the embodiments of the disclosure, the overall yield in recovery of the one or more steviol glycosides may increase by at least 10%, such as 15%, 20%, 25%, 30%, 35%, 40%, 45%, 50%, 55%, 60%, 65%, 70%, 80%, 85%, 90%, or 95%. In the embodiments of the disclosure, the overall yield may increase to up to 40%, such as 45%, 50%, 55%, 60%, 65%, 70%, 80%, 85%, 90%, or 95% overall yield.

General Definitions

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows. The articles "a" and "an"

are used herein to refer to one or to more than one (i.e. to one or at least one) of the grammatical object of the article. By way of example, "an element" may mean one element or more than one element.

The word "about" or "approximately" when used in association with a numerical value (e.g. about 10) preferably means that the value may be the given value (of 10) more or less 10%, or more or less 5% of the value.

Steviol glycoside is herein defined as any of steviolmonoside, steviolbioside, rubusoside, dulcoside B, dulcoside A, rebaudioside B, rebaudioside G, stevioside, rebaudioside C, rebaudioside F, rebaudioside A, rebaudioside I, rebaudioside E, rebaudioside H, rebaudioside L, rebaudioside K, rebaudioside J, rebaudioside M, rebaudioside M2, rebaudioside D, rebaudioside D2, rebaudioside N, rebaudioside O, rebaudioside A, other steviol glycosides found in *Stevia rebaudiana* Berton ior a synthetic steviol glycoside. A preferred steviol glycoside of to the disclosure is rebaudioside M (Reb-M).

The term "recombinant" when used in reference to a nucleic acid, or protein indicates that the nucleic acid, or protein has been modified in its sequence if compared to its native form by human intervention. The term "recombinant" when referring to a cell indicates that the genome of the cell has been modified in its sequence if compared to its native form by human intervention. The term "recombinant" is synonymous with "genetically modified".

A nucleic acid construct or polynucleotide as disclosed herein can be introduced into a cell such as a prokaryotic or eukaryotic cell via conventional transformation or transfection techniques. As used herein, the terms "transformation" and "transfection" are intended to refer to a variety of art-recognized techniques for introducing foreign nucleic acid (e.g. DNA) into a recombinant cell well known to those skilled in the art.

A "cell" as defined herein is an organism suitable for genetic manipulation and which may be cultured at cell densities useful for industrial production of a target product. A suitable organism may be a microorganism, for example one which may be maintained in a fermentation device. With regard to the present disclosure, it is understood that organisms, such as e.g. microorganisms, fungi, algae or plants also include synonyms or basonyms of such species having the same physiological properties, as defined by the International Code of Nomenclature of Prokaryotes or the International Code of Nomenclature for algae, fungi, and plants (Melbourne Code). A cell may be a cell found in nature or a cell derived from a parent cell after genetic manipulation or classical mutagenesis.

As used herein, a recombinant cell is one which is genetically modified or transformed/transfected with one or more of the nucleotide sequences as defined herein. The presence of the one or more such nucleotide sequences alters the ability of the microorganism to produce steviol or a steviol glycoside, in particular one or more steviol glycosides. A non-recombinant cell, i.e. one that is not transformed/transfected or genetically modified, typically does not comprise one or more of the nucleotide sequences enabling the cell to produce a steviol glycoside. Hence, a non-recombinant cell is typically a cell that does not naturally produce a steviol glycoside, although a cell which naturally produces a steviol or a steviol glycoside and which has been modified according to the disclosure is considered a recombinant cell according to the disclosure.

A recombinant cell, interchangeably referred to as a host cell, in the embodiments of the disclosure may be, for example, a multicellular organism or a cell thereof or a unicellular organism. A recombinant cell may be a prokaryotic, archaebacterial or eukaryotic cell.

A prokaryotic host cell may, but is not limited to, a bacterial host cell. A eukaryotic host cell may be, but is not limited to, a yeast, a fungus, an amoeba, an algae, an animal, an insect host cell.

A eukaryotic host cell may be a fungal host cell.

A eukaryotic cell may be a fungus, such as a filamentous fungus or yeast.

Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasmsonia, Thermoascus, Thielavia, Tolypocladium, Trametes* and *Trichoderma.* Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla.*

A eukaryotic host cell may be a yeast cell. Preferred yeast host cells may be selected from the genera: *Saccharomyces* (e.g., *S. cerevisiae, S. bayanus, S. pastorianus, S. carlsbergensis*), *Brettanomyces, Kluyveromyces, Candida* (e.g., *C. krusei, C. revkaufi, C. pulcherrima, C. tropicalis, C. utilis*), *Issatchenkia* (e.g. *I. orientalis*) *Pichia* (e.g., *P. pastoris*), *Schizosaccharomyces, Hansenula, Kloeckera, Pachysolen, Schwanniomyces, Trichosporon, Yarrowia* (e.g., *Y. lipolytica* (formerly classified as *Candida lipolytica*)), *Yamadazyma.*

Prokaryotic host cells may be bacterial host cells. Bacterial host cell may be Gram negative or Gram-positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus*), *Acinetobacter, Nocardia, Xanthobacter, Escherichia* (e.g., *E. coli* (e.g., strains DH 1 OB, Stbl2, DH5-alpha, DB3, DB3.1), DB4, DBS, JDP682 and ccdA-over (e.g., U.S. application Ser. No. 09/518, 188))), *Streptomyces, Erwinia, Klebsiella, Serratia* (e.g., *S. marcessans*), *Pseudomonas* (e.g., *P. aeruginosa*), *Salmonella* (e.g., *S. typhimurium, S. typhi*). Bacteria also include, but are not limited to, photosynthetic bacteria (e.g., green non-sulfur bacteria (e.g., *Choroflexus* bacteria (e.g., *C. aurantiacus*), *Chloronema* (e.g., *C. gigateum*)), green sulfur bacteria (e.g., *Chlorobium* bacteria (e.g., *C. limicola*), *Pelodictyon* (e.g., *P. luteolum*), purple sulfur bacteria (e.g., *Chromatium* (e.g., *C. okenii*)), and purple non-sulfur bacteria (e.g., *Rhodospirillum* (e.g., *R. rubrum*), *Rhodobacter* (e.g. *R. sphaeroides, R. capsulatus*), and *Rhodomicrobium* bacteria (e.g., *R. vanellii*)).

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present disclosure is further illustrated by the following non-limiting examples:

EXAMPLES

Example 1. Solubilization of Steviol Glycosides Precipitated in the Fermentation Broth

Introduction

With improving productivity of strains and increasing titres of steviol glycosides such as Reb-A and Reb-M in fermentation broth, part of the steviol glycosides may precipitate during the course of the fermentation. This precipitation is visible as a white layer on top of the cell pellet after centrifugation of the broth (see FIG. 1). Such precipitation is undesirable from Down Stream Processing (DSP) perspective since only solubilized product can be processed further on in the DSP process. A process was developed wherein the precipitated steviol glycosides in the fermentation broth are re-solubilized while the lysis of host cells was substantially prevented.

Materials and Methods

A fermentation broth comprising steviol glycosides, including Reb-M, was provided essentially according to the method described in WO2015007748.

The fermentation broth was subjected to a heat shock for 90 seconds at different temperatures between 45 and 90 degrees Celsius. Subsequent to the heat shock, the fermentation broth was subjected to centrifugation to separate the cells from the supernatant comprising the steviol glycosides. The amount of cell-lysis was determined by measuring the increase of dry weight of the supernatant as well as by measuring the pellet volume. The amount of Reb-M in the supernatant was determined using LC-UV.

Ultrafiltration tests were performed on the supernatant of the heat shocked samples to determine whether the heat shock influenced ultrafiltration performance. Before ultrafiltration, the pH of the supernatant samples was adjusted to pH 3.5, the supernatant samples were incubated for two hours at 70 degrees Celsius and cleared by centrifugation at 60 degrees Celsius and 7000 g for 20 minutes.

Results

The results of the heat shock of the fermentation broth for 90 seconds at different temperatures between 45 and 90 degrees Celsius are depicted in Table 1 here below.

TABLE 1

| Heat shock temperature (° C.) | Pellet volume Before heat shock | Pellet volume After heat shock | Observations |
|---|---|---|---|
| 45 | 40% | 40% | Still a white intermediate layer, temperature/time is not sufficient |
| 50 | 40% | 40% | Still a white intermediate layer, temperature/time is not sufficient |
| 55 | 40% | 38% | Still a white intermediate layer, pellet volume starts decreasing |
| 60 | 38% | 38% | White layer disappeared |
| 75 | 40% | 26% | White layer disappeared |
| 85 | 40% | 26% | White layer disappeared |
| 95 | 40% | 26% | White layer disappeared |

Heating at 60° C. resulted in the disappearance of the intermediate layer, i.e. re-solubilization of the steviol glycosides. Above 60° C., substantial cell lysis occurred, indicated by the decrease in cell pellet volume. Heating to 60° C. was repeated twice to demonstrate the repeatability and to corroborate the observed yield increase. The results are depicted in Table 2.

TABLE 2

| Heat shock temperature (° C.) | Pellet volume Before heat shock | Pellet volume After heat shock | Dry matter Broth | Dry matter Supernatant | Dry matter yield Percentage dry matter in supernatant |
|---|---|---|---|---|---|
| 30 (control) | 40% | 40% | 11.30% | 3.87% | 34.2 |
| 60 | 40% | 38% | 11.21% | 3.88% | 34.6 |
| 60 | 40% | 35% | 11.30% | 3.95% | 35.0 |

Although the pellet volume decreased 2-5%, thus indicating some cell lysis, the increase in dry matter in the supernatant was minimal, indicating little influence of the cell lysis to the overall. Ultrafiltration fluxes of the supernatants were normal after 60° C. heat shock. At higher temperatures, ultrafiltration fluxes decreased dramatically. The overall yield in steviol glycoside recovery increased by 40%-60% to an overall 90%-95% when using a heat shock for re-solubilization of precipitated steviol glycosides.

In a follow-up experiment, it was determined that the duration of the heat shock of the fermentation broth could be shortened to 30 seconds, which was sufficient dissolve all precipitated steviol glycosides (data not shown).

The invention claimed is:

1. A process for the production of one or more steviol glycosides, the process comprising:
   culturing recombinant cells capable of producing the one or more steviol glycosides in a culture medium to provide a culture broth comprising the culture medium and the recombinant cells, wherein the one or more steviol glycosides are produced and precipitate out of the culture broth; and
   heating the culture broth comprising the recombinant cells to 45-65° C. for a period of at most 90 seconds such that the precipitated one or more steviol glycosides are at least partially re-solubilized in the culture broth.

2. The process according to claim 1, wherein lysis of the recombinant cells in the culture broth is reduced as compared to a culture broth comprising recombinant cells heated to a temperature greater than 65° C., or heated to 45-65° C. for more than 90 seconds.

3. The process according to claim 1, wherein the heating is performed at 45-65° C. for at most 90 seconds, under which conditions the one or more steviol glycosides are completely re-solubilised in the culture broth.

4. The process according to claim 1 wherein the heating is performed at a temperature of 60-65° C. and for a period of at most 60 seconds.

5. The process according to claim 1, wherein the heating is performed using a heat plate exchanger.

6. The process according to claim 5, wherein the one or more steviol glycosides present in the culture broth are separated from the recombinant cells by centrifugation and wherein the centrifuge is optionally operably linked to the heat plate exchanger.

7. The process according to claim 1, wherein the one or more steviol glycosides present in the culture broth are recovered and optionally purified.

8. The process according to claim 7, wherein recovering and optionally purifying the one or more steviol glycosides comprises one or more of a filtration, an ultra-filtration, an evaporation, a crystallisation, and a heat shock of the culture broth from which the recombinant cells have been removed.

9. The process according to claim 1, further comprising removal of the recombinant cells from the culture broth after the heating.

10. The process according to claim 6, wherein the one or more steviol glycosides present in the culture broth are separated from the recombinant cells by centrifugation at most 40,000 g*minute, and wherein centrifugation time is optionally at most 5 minutes.

11. The process according to claim 1, wherein the one or more steviol glycosides is reb M, reb D, reb A, reb B or a mixture of these steviol glycosides.

12. The process according to claim 1, wherein the recombinant cells are capable of producing steviol glycosides and wherein said recombinant cells comprise one or more nucleic acid sequences encoding one or more of:

a polypeptide having hydroxymethylglutaryl-CoA reductase activity;

a polypeptide having farnesyl-pyrophosphate synthetase activity;

a polypeptide having geranylgeranyl diphosphate synthase activity;

a polypeptide having ent-copalyl pyrophosphate synthase activity;

a polypeptide having ent-Kaurene synthase activity;

a polypeptide having ent-Kaurene oxidase activity;

a polypeptide having kaurenoic acid 13-hydroxylase activity;

a polypeptide having NADPH-cytochrome p450 reductase activity;

a polypeptide having UGT74G1 activity;

a polypeptide having UGT2 activity;

a polypeptide having UGT85C2 activity; and a polypeptide having UGT76G1 activity.

13. The process according to claim 1, wherein the recombinant cells belong to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*, optionally the recombinant cells are *Saccharomyces cerevisiae* cells, *Yarrowia lipolytica* cells, *Candida krusei* cells, *Issatchenkia orientalis* cells, or *Escherichia coli* cells.

14. The process according to claim 1, wherein the one or more steviol glycosides is reb M, reb D or a mixture thereof.

15. The process according to claim 1, wherein the culture broth is heated to 60° C. to 65° C. for a period of at most 90 seconds.

16. The process according to claim 1, wherein the culture broth is heated to 60° C. to 65° C. for a period of at most 30 seconds.

17. A process for the recovery of one or more steviol glycosides from a culture broth wherein said culture broth comprises:

recombinant cells capable of producing one or more steviol glycosides, a culture medium, one or more precipitated steviol glycosides, and optionally one or more solubilised steviol glycosides, wherein the process comprises heating the culture broth to 45-65° C. for a period of at most 90 seconds such that the precipitated one or more steviol glycosides are re-solubilized in the culture broth.

* * * * *